(12) United States Patent
Braune et al.

(10) Patent No.: US 8,536,366 B2
(45) Date of Patent: Sep. 17, 2013

(54) FORMATION OF NITRATE ESTERS IN MICROREACTORS AND MILLIREACTORS USING A CONTINUOUS PRODUCT EXTRACTION IN A TURBULENT FLOW REGIME

(75) Inventors: Sascha Braune, Luftenberg an der Donau (AT); Stefan Steinhofer, Gurten (AT); Peter Poechlauer, Linz (AT); Rafael Wilhelmus E. G. Reintjens, Maaseik (BE); Nicole Theodora W. Linssen, Kessenich (BE); Mehul Thathagar, Geleen (NL)

(73) Assignee: DSM Fine Chemicals Austria NFG GmbH & Co KG, Linz (AT)

( * ) Notice: Subject to any disclaimer, the term of this patent is extended or adjusted under 35 U.S.C. 154(b) by 416 days.

(21) Appl. No.: 12/808,829

(22) PCT Filed: Dec. 19, 2008

(86) PCT No.: PCT/EP2008/068034
§ 371 (c)(1),
(2), (4) Date: Oct. 26, 2010

(87) PCT Pub. No.: WO2009/080755
PCT Pub. Date: Jul. 2, 2009

(65) Prior Publication Data
US 2011/0034720 A1    Feb. 10, 2011

(30) Foreign Application Priority Data
Dec. 20, 2007  (EP) .................................. 07024754

(51) Int. Cl.
C07C 201/02 (2006.01)
C07C 201/16 (2006.01)
B01J 14/00 (2006.01)
B01D 11/04 (2006.01)

(52) U.S. Cl.
USPC ........... 558/480; 210/638; 366/336; 366/338; 422/129; 422/224; 422/603; 558/488; 585/924

(58) Field of Classification Search
USPC ................. 210/634, 638, 639; 366/336, 338, 366/341, DIG. 3; 558/480–488; 585/921–926; 422/129, 131, 224, 225, 603
See application file for complete search history.

(56) References Cited

U.S. PATENT DOCUMENTS
5,089,652 A * 2/1992 Sohara et al. ................. 558/480
6,362,311 B1 * 3/2002 Highsmith et al. ........... 528/409
(Continued)

FOREIGN PATENT DOCUMENTS
WO  WO 2004/043897  5/2004
WO  WO 2004/043898  5/2004
WO  WO 2005/077883  8/2005

OTHER PUBLICATIONS
International Search Report for PCT/EP2008/068034, mailed May 11, 2009.
(Continued)

Primary Examiner — Joseph Drodge
(74) Attorney, Agent, or Firm — Nixon & Vanderhye P.C.

(57) ABSTRACT

A process for the continuous production of a compound of Formula (II), HO—$R^1$—$ONO_2$ (II) wherein $R^1$ is a straight chain alkyl radical having from 3 to 6 carbon atoms, in a two-phase solvent system, comprising contacting a compound of Formula (I), HO—$R^1$—OH (I) wherein $R^1$ is as defined above, with nitric acid in the presence of a first solvent, wherein the compound of Formula (II) is continuously extracted into a second solvent, and the reaction is carried out in a mixing microreactor which provides a power loss of at least 1.3 times the power loss provided under identical conditions by a circular cross-section straight-channel microreactor having an internal diameter equal to the average hydraulic diameter of the mixing microreactor and a length equal to the length of the mixing microreactor.

11 Claims, 2 Drawing Sheets

(56) References Cited

U.S. PATENT DOCUMENTS

| | | | |
|---|---|---|---|
| 6,806,087 B2* | 10/2004 | Kibby et al. | 436/37 |
| 7,098,357 B2* | 8/2006 | Wurziger et al. | 558/315 |
| 8,206,597 B2* | 6/2012 | Yang et al. | 210/767 |
| 2005/0234123 A1* | 10/2005 | Belli et al. | 514/509 |
| 2005/0276160 A1* | 12/2005 | Woehl et al. | 366/336 |
| 2006/0128983 A1* | 6/2006 | Francescutti et al. | 558/480 |
| 2006/0135806 A1* | 6/2006 | Scubla et al. | 558/484 |
| 2007/0287852 A1* | 12/2007 | Antes et al. | 558/480 |
| 2008/0281090 A1* | 11/2008 | Lee et al. | 536/122 |

OTHER PUBLICATIONS

Written Opinion of the International Searching Authority for PCT/EP2008/067034, mailed May 11, 2009.

Ehrfeld, W. et al., "Ullmann's Encyclopedia of Industrial Chemistry $6^{th}$ Ed.", Microreactors, vol. 22, (Jan. 1, 2003), pp. 1-30.

* cited by examiner

FORMATION OF NITRATE ESTERS IN MICROREACTORS AND MILLIREACTORS USING A CONTINUOUS PRODUCT EXTRACTION IN A TURBULENT FLOW REGIME

This application is the U.S. national phase of International Application No. PCT/EP2008/068034 filed 19 Dec. 2008, which designated the U.S. and claims priority to EP Application No. 07024754.9 filed 20 Dec. 2007, the entire contents of each of which are hereby incorporated by reference.

The reaction of monohydric and polyhydric alcohols with nitrating agents such as nitric acid or nitrating acid gives the corresponding nitrate esters, e.g. glyceryl trinitrate from glycerin (cf. Winnacker, Küchler, "Chemische Technologie", volume 7, 1986, pages 359 to 402). The preparation and handling of nitrate esters is however problematical from a safety point of view and places severe demands on the producer, especially because a majority of such products are declared as explosive materials. A problem in handling nitration of glycols is that both mono-(i.e. partially nitrated) and dinitrates, and the glycol starting material itself, may be oxidized by the strong oxidizing agent nitric acid. Such oxidation liberates $CO_2$, $H_2O$ and $N_2$ and can escalate exponentially, leading to potentially dangerous explosion. WO2005/077883 describes a process for preparing liquid nitrate esters in microreactors.

A particular challenge is the selective reaction of individual hydroxy groups, for example of glycols and their homologues, to form the mono-esterified compounds. Thus, under the homogeneous reaction conditions of WO2005/077883, virtually exclusively the multiply esterified products are obtained.

A laboratory process for the selective preparation of relatively small amounts of nitrate esters from polyols using the extraction principle is described by Michael W. Barnes et al. in Synthesis 1977, 484-485.

Further, WO2004/04328 describes a batch reaction process for mononitration of butanediol. The reaction is carried out at temperatures from −5° C. to 2° C. in dichloromethane. The nitration reaction is quenched with water and the mononitrated product later separated from the dinitrate and the unreacted butanediol.

Rosaguti et al., in Chem. Eng. Technol. 2005, 28 (3); 353-361, describe the flow characteristics of a fluid in a heat exchanger having a serpentine channel, with a circular cross-section. The phenomenon of Dean vortices are described. These are created by the bends in the channel and contribute to turbulence of the fluid, thereby increasing heat transfer to the walls of the channel. Accordingly, improved heat transfer from the fluid in the heat exchanger is provided. Rosaguti et al., also teach that Dean vortex formation imposes a "pressure drop penalty" on the system. The pressure drop of a given flow through a pipe of given length and hydraulic diameter rises if the pipe contains bends capable of inducing Dean vortices under the given flow conditions.

A microreactor is a reactor having one or more characteristic dimensions in the micrometer to millimeter scale. Descriptions of microreactors may be found, for example, in: V. Hessel and H. Löwe, "Mikroverfahrenstechnik: Komponenten, Anlagen-konzeption, Anwenderakzeptanz", Chem. Ing. Techn. 74, 2002, pages 17-30, 185-207 and 381-400. S. Löbbecke et al., "The Potential of Microreactors for the Synthesis of Energetic Materials", 31$^{st}$ Int. Annu. Conf. ICT; Energetic Materials-Analysis, Diagnostics and Testing, 33, 27-30 Jun. 2000, Karlsruhe, Germany. In publications which discuss microreactors and processes in microreactors, the advantages of laminar flow are particularly emphasized. This is highlighted as a critical factor for successfully carrying out reactions. Reynolds numbers significantly below 1000 are greatly desired in the prior art.

Microreactors, micromixers, micro-heat-exchangers have been developed, for example in Germany (i.e.: IMM, Mainz, and Forschungszentrum Karlsruhe) and in the USA (i.e.: MIT and DuPont).

A problem associated with the use of multi-phase systems in continuous reactors, particularly microreactors, is that of mixing of the two phases. Movement of fluids through a reactor typically occurs by Taylor flow or slug flow. This causes alternating discrete regions of each phase, which flow through the reactor at the same rate, allowing a certain degree of mass transfer.

It is an object of the present invention to develop an efficient process for the selective preparation of a mononitrate ester of a glycol.

It has surprisingly been found by the present inventors that reaction of glycols with nitric acid to selectively form mononitrate esters may be carried out efficiently and safely in a continuous process by utilizing a two-phase solvent system to extract the mononitrated product into a second solvent from reaction in a first solvent. The reaction conditions make use of turbulence generated in a mixing microreactor to ensure adequate dispersion of the immiscible solvents and improve mass transfer of the mononitrated product from the first solvent to the second solvent. Reaction is carried out on the microreactor scale to ensure efficient heat transfer from the reaction. By the process of the present invention particularly high yields and throughput can be achieved while effectively transferring heat to control potentially dangerous side reactions.

Accordingly, the present invention provides a process for the continuous production of a compound of Formula (II),

HO—R$^1$—ONO$_2$ (II)

wherein R$^1$ is a straight chain alkyl radical having from 3 to 6 carbon atoms, in a two-phase solvent system, comprising contacting a compound of Formula (I),

HO—R$^1$—OH (I)

wherein R$^1$ is as defined above,
with nitric acid in the presence of a first solvent,
wherein the compound of Formula (II) is continuously extracted into a second solvent, and the reaction is carried out in a mixing microreactor which provides a power loss of at least 1.3 times the power loss provided under identical conditions by a circular cross-section straight-channel microreactor having an internal diameter equal to the average hydraulic diameter of the mixing microreactor and a length equal to the length of the mixing microreactor.

As used herein, a microreactor means a micro- or minireactor. Each of these differ only from conventional size reactors in the dimensions and constructions of the reaction channel structures. A microreactor is a miniaturized reactor with characteristic dimensions (channel width and depth, or plate width) in micrometers to millimeters. The characteristic dimensions are the dimensions perpendicular to the flow of the reaction mixture through the microreactor. The characteristic dimensions are for example from 0.01 mm to 10 mm; typically from 0.5 to 6 mm, for example 3.5 to 5 mm.

Preferably, a microreactor is defined as a reactor having a channel with a hydraulic diameter of 20 mm or less. The hydraulic diameter $D_h$ is defined as 4A/U, wherein A is the cross sectional area of the reactor channel and U is the perimeter of said cross section. More preferably the hydraulic diameter is from 0.01 mm to 10 mm; more preferably from 0.5 to 6 mm, more preferably from 3.5 to 5 mm, or 1, 2, 3, or 4 mm.

For a round tube, the hydraulic diameter $D_h$ equals the diameter of the tube. For a rectangular duct, that has a cross section with a rectangular shape, the hydraulic diameter equals $4LW/2(L+W)$, wherein L is the length of the longest side of the rectangle and W is the width of the rectangle. For the special case of a square duct, the hydraulic diameter $D_h$ equals L. For an annulus, the hydraulic diameter is $D_h = (4 \cdot 0.25\pi(D_o^2-D_i^2))/\pi(D_o-D_i) = D_o-D_i$, wherein $D_o$ is the outer diameter of the annulus and $D_i$ is the inner diameter. However, it should be noted that the general formula 4A/U, wherein A is the cross sectional area of the reactor channel and U is the perimeter of said cross section, allows calculation of the hydraulic diameter for any shape of reactor channel. The hydraulic diameter may vary along the length of the microreactor.

A mixing microreactor is a microreactor as defined above which provides mixing energy to a fluid (for example the two-phase solvent system) passing through it.

Power loss, or $\Delta W$ [$Js^{-1}$], is the amount of power (energy per unit time) lost by a fluid passing through the microreactor. It may be represented by the following equation: $\Delta W=\Delta PF$, where $\Delta P$ [$Nm^{-2}$] is the difference in pressure between an inlet and an outlet of the mixing microreactor. It is measured by a pressure gauge at each of the inlet and outlet of the mixing microreactor; and F is flow rate [$m^3s^{-1}$] of fluid flowing through the mixing microreactor.

As described herein power loss consists of two components: a straight channel power loss, $\Delta W_S$, and mixing energy, $\Delta W_M$.

Straight channel power loss, $\Delta W_S$, is the power loss of a fluid flowing through a circular cross-section straight-channel microreactor having an internal diameter equal to the average hydraulic diameter of the mixing microreactor and a length equal to the length of the mixing microreactor. In such a system, $\Delta W=\Delta W_S$, i.e. there is no $\Delta W_M$.

Mixing power, $\Delta W_M$, is that part of power loss due to generating vortices and engulfment flow that results in mixing of fluid passing through the mixing microreactor. This may be defined as the difference between power loss and straight channel power loss, i.e. $\Delta W_M=\Delta W-\Delta W_S$. This is caused by the internal geometry of the mixing microreactor. For a given system, mixing energy can be calculated by:

i) measuring difference in pressure between inlet and outlet of a mixing microreactor, $\Delta W$;

ii) measuring the difference in pressure between inlet and outlet of a circular cross-section straight-channel microreactor having an internal diameter equal to the average hydraulic diameter of the mixing microreactor and a length equal to the length of the mixing microreactor, $\Delta W_S$; and iii) subtracting $\Delta W_S$ from $\Delta W$ to give $\Delta W_M$.

In principle the internal geometry of the mixing microreactor may take any form provided $\Delta W \geq 1.3 \Delta W_S$. Preferably $\Delta W \geq 1.5 \Delta W_S$. More preferably $\Delta W \geq 2\Delta W_S$, for example $\Delta W \geq 3\Delta W_S$.

In other words, preferably the mixing microreactor provides a power loss of at least 1.5 (more preferably at least 2, still more preferably at least 3) times the power loss provided under identical conditions by a circular cross-section straight-channel microreactor having an internal diameter equal to the average hydraulic diameter of the mixing microreactor and a length equal to the length of the mixing microreactor.

Preferred internal geometry is waveform, for example serpentine, helical or zig zag. The external shape of the mixing microreactor may follow the internal shape of the mixing microreactor or a different geometry. In its simplest form the mixing microreactor is a tube, which is deformed, for example by bending or pinching.

As used herein waveform includes any waveform, including, square, trapezoidal, sinusoidal and round. The waveform may operate in two dimensions or three. It may be irregular or regular. Serpentine means a tube oscillating in two dimensions with a round or sinusoidal waveform. The form may trace any waveform, including, square, trapezoidal, sinusoidal and round. Helical means a channel at least approximately tracing a spiral shape. Zig zag is a preferred type of waveform combining alternating straight sections and bends. A zig zag typically occurs in two dimensions and comprises alternating straight sections of equal length and bends of equal angle.

The cross-sectional shape of the mixing microreactor may vary along the length of the reactor. For example, it may oscillate. One example of a mixing microreactor suitable for use in the present invention is a circular cross-sectional tube, pinched at intervals to form an elipse at the points of pinching. Similarly the hydraulic diameter may vary along the length of the reactor. For example, it may oscillate.

Figure 4:
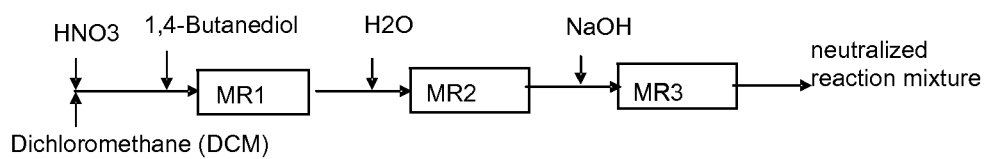

FIG. 4 depicts an example of apparatus set-up for the process of the present invention. MR1 is a mixing microreactor; MR2 and MR3 are microreactors. In this typical reactor set up $HNO_3$ and dichloromethane are mixed in a T-mixer; 1,4-butanediol is added and reaction is carried out in the mixing microreactor; water is added to quench the reaction in a second reactor; and NaOH is added to neutralise the reaction mixture in a third microreactor.

Flow under identical conditions means that all conditions acting on the two-phase solvent system, except for the reactor itself are identical. This includes temperature, input pressure, flow rate and concentration of reagents.

A circular cross-section straight-channel microreactor having an internal diameter equal to the hydraulic diameter of the mixing microreactor and an equal length to the length of the mixing microreactor is essentially a fixed diameter circular tube.

Length of the mixing microreactor is taken to be the distance from the inlet to the outlet by following a path through the centre of mass defined by the space inside the mixing microreactor. The length of the channels depends on the desired residence time, which may vary, for example from 0.01 sec to 1000 sec, and is preferably from 0.5 sec to 200 sec, more preferably from 1 sec to 100 sec, more preferably 10 sec to 80 sec Average hydraulic diameter is defined as the mean value of the hydraulic diameter of the mixing microreactor. In practice this may be approximated by calculating the hydraulic diameters sampled at 1 cm, preferably 1 mm, intervals along the length of the mixing microreactor.

The mixing microreactor used in the process of the present invention, comprises an inlet for receiving a feed stream and an outlet for emitting a product stream. The reactants are contacted with each other in the mixing microreactor, allowing a chemical reaction to take place in a narrow confined space, such as a channel. Dimensions of the micro reactor are chosen in such a way that the characteristic times for heat transfer and/or mass transfer are very low. Therefore high rates of reaction and heat transfer can be handled in a controlled fashion. The heat is transferred to or from a heat transfer fluid that does not come into contact with the reactants or the products.

A number of mixing microreactors may be combined in parallel to form a microstructured reactor. Entering reactants are distributed over manifold systems or other distribution systems to the individual microreactors. Each micro-structured reactor may include mixing zones to mix the entering reactants and/or the reaction medium. Each micro-structured reactor may contain residence zones to allow the reaction medium to obtain sufficient conversion. The micro-structured reactor may be constructed of, or may contain, a number of parallel sub-units (mixing zones with residence zones) in a numbering-up concept to obtain sufficient production capacity. An example is a multi channel monolith reactor for example.

The process of the present invention is preferably performed in multi channel micro structured reactor, such as for example a monolith reactor, a HEX reactor or a printed circuit heat exchange reactor.

A microreactor provides high mass transfer and high heat transfer capacity to the reaction. By carrying out the process in a microreactor, safety concerns are reduced and the existence of hazardous conditions minimized. The danger of explosion is eliminated or at least the risks of explosions are drastically reduced. In fact, one advantage of using a microreactor is that it permits harsher conditions to be used, for example higher temperatures and higher concentration of reagents. This increases the yield of the reaction and makes the use of less efficient catalysts economically more feasible than for example the previously known more efficient rhodium complex catalysts.

The compound of Formula (I) is preferably 1,3-propanediol or 1,4-butanediol.

The reaction of the compound of formula (I) with nitric acid occurs in a first solvent. The first solvent is typically hydrophilic, and is preferably water.

The second solvent is typically hydrophobic. Suitable second solvents are organic solvents (for example a hydrophobic extraction phase) in which the compound of formula (II) (the desired product mononitrate ester) has high solubility and which is inert under the reaction conditions. Preferred second solvents are halogenated hydrocarbons such as dichloromethane and tetrachloroethane.

As a result of the high solubility of the desired product in the organic solvent used, the product can be withdrawn from the strongly acidic nitration conditions and oxidation conditions. Accordingly the formation of the undesired dinitrate and of oxidation products, which would occur in the first solvent, is significantly suppressed or prevented.

Reynolds numbers of greater than 200 are sought in the mixing microreactor. Preferably the Reynolds number is between 400 and 2000, more preferably from 500 to 1,500, still more preferably from 600 to 1000.

Under the conditions, a particularly fine and stable emulsion of the reaction mixture may be formed. Undesirable secondary reactions such as oxidations of starting materials and products can be suppressed in this way.

Secondary reactions such as oxidations present a problem for the nitration of glycols because they can liberate a great deal of energy. In a mixing microreactor, this can be effectively removed or controlled due to a very high surface area/volume ratio of the mixing microreactor. Accordingly efficient heat transfer provided by the mixing microreactor reduces the risk of a runaway side reaction which might otherwise cause explosion.

Acidic phases of the two-solvent system mixture, which frequently tend to decompose spontaneously in an autocatalytic fashion, have been found to be particularly hazardous. Nitric acid is a powerful oxidizing agent and can oxidize the glycol, and mono and dinitrate products, leading to explosion. To reduce this hazard, which cannot be controlled in batch processes, the two-phase reaction mixture is preferably neutralised in the mixing microreactor or in a subsequent microreactor. The neutralized reaction phases, having $pH \geqq 7$, now merely contains the thermal decomposition potential of the nitrate esters formed. Preferably the process of the present invention further comprises the subsequent step of neutralizing the two-phase solvent system by adjusting the pH to at least 7. This subsequent neutralizing step may be carried out in a subsequent microreactor.

The small working volume of the mixing microreactor reduces the quantities of hazardous substances which have to be handled to a minimum. Accordingly, should explosion occur, the present process is more safe than a batch process.

The effective mixing of the two solvents by use of a mixing microreactor further acts to reduce the likelihood of explosion, since the mononitrate ester is effectively transferred to the second solvent, and away of contact from the nitric acid. Thus the concentration of oxidisable material in the first solvent is reduced.

As a result of short residence and reaction times obtainable in the process of the present invention, and control of the residence time, reactions can be carried out at temperatures which cannot be achieved in a batch process. Increased temperature allows a faster rate of reaction compared with the batch process and therefore higher throughput of the reagents. Temperatures from 0° C. to 90° C. can be achieved. Preferred temperatures are from 10° C. to 60° C., more preferably from 30° C. to 50° C., particularly preferably about 40° C.

Typically the pressure at the inlet of the mixing microreactor is from 1 to 50 bar, preferably 2 to 30 bar, more preferably 5 to 20 bar.

In a preferred embodiment, the present invention provides a process for the continuous preparation of mononitrate esters, wherein a compound of the formula I

HO—R1-OH                                    (I)

where R1 is a straight-chain alkyl radical having from 3 to 6 carbon atoms, is reacted with nitric acid in the presence of a solvent in two-phase turbulent flow in a microreactor to form the corresponding mononitrate ester, with the reaction product being extracted continuously, and the two-phase reaction mixture is neutralized directly in the microreactor or in a second microreactor.

Typically the advantage of increased turbulence over the straight line microreactor increases with flow rate. Typically flow rate is greater than 0.1 $ms^{-1}$, preferably greater than 0.2 $ms^{-1}$, more preferably greater than 0.3 $ms^{-1}$, for example from 0.5 to 5 $ms^{-1}$.

The phenomenon of Dean vortices is used in the mixing microreactor to effect high mixing of the two solvents. This overcomes the problem of poor mixing due to Taylor flow or slug flow. High mixing increases extraction of the compound of formula (II) into the second solvent before it is further nitrated to a dinitroester. This delivers a high yield of product in high selectivity. The phenomenon is measurable by pressure drop in the apparatus, as described herein.

To achieve an efficient extraction of the desired nitrate ester product from the first solvent (for example an acidic hydrophilic reaction phase) into the second solvent (for example a hydrophobic extraction phase), nitric acid solution having a concentration of from 65% to 90%, preferably from 75% to 90%, particularly preferably 80-85%, are used.

Typically, the nitric acid is stabilized before use. By stabilized is meant that, for example, nitrogen oxides in any form and nitrites are removed by reaction with a stabiliser, for example, urea.

Typically, prior to reaction, urea is added to the nitric acid until the latter is colorless. Preferably from 0.1 to 3% by weight of urea is added, more preferably from 0.5 to 1.5% by weight, particularly preferably 1% by weight.

To achieve effective mass transfer between the hydrophilic hydrophobic phases, the production and stabilisation of a very fine emulsion is important. A fine emulsion can most readily be achieved by means of turbulent flows which have Reynolds numbers above 1000, preferably above 2000, particularly preferably about 2500.

A module to effectively stop the reaction by means of water and cool the reaction mixture to below 10° C.

Three further mixing modules to set the two-phase reaction mixture to a pH of >7 by means of a base.

Possibly further heat exchanger modules between the individual additions of base in order to be able to remove sufficient energy. The temperature should be kept at not more than 25° C., better below 10° C., during the neutralization in order to suppress by-product formation.

Mononitroesterification of 1,4-butanediol was carried out. Dichloromethane is used as solvent and 85% strength nitric acid stabilized with urea is used as nitrating agent.

For comparison, the percentages by weight of 1,4-butanediol mononitrate and 1,4-butanediol dinitrate in the organic phase after neutralization are determined by means of gas chromatography. Results and conditions are summarized in Table 1 below.

TABLE 1

Comparison of the results for laminar and turbulent flow

|  |  | Laminar flow | Turbulent flow | Turbulent flow, optimized | Laminar flow |
|---|---|---|---|---|---|
| 85% strength nitric acid | [g/min] | 6.8 | 6.8 | 50.0 | Not able to be |
| Dichloromethane | [g/min] | 13.5 | 13.5 | 55.0 | realized, since |
| 1,4-Butanediol | [g/min] | 1.5 | 1.5 | 4.5 | oxidations |
| Water | [g/min] | 10 | 10 | 20.0 | occur |
| Sodium hydroxide | [g/min]/conc. | 10.5/5% | 10.5/5% | 22.0 | preferentially. |
| Sodium hydroxide | [g/min]/conc. |  |  | 44.0 |  |
| Sodium hydroxide | [g/min]/conc. |  |  | 44.0 |  |
| Residence time | [sec] | 96 | 96 | 24.0 |  |
| Yield of 1,4-butanediol mononitrate | [%] | 3 | 12.2 | 56.1 |  |
| Yield of 1,4-butanediol dinitrate | [%] | 0 | 3.5 | 16.4 |  |
| Selectivity based on formation of nitrated products | [%] | 97.5 | 99.9 | 99.8 |  |

As a result of the extraction of the nitrate ester which has been obtained selectively into the hydrophobic extraction phase, the ester is withdrawn from the acidic esterification conditions of the hydrophilic phase and can be obtained with high selectivity and high yield.

This principle of extractive removal of the desired product from the reaction phase into an extraction phase in a microreactor can also be applied to other reactions, for example the selective protection of alcohols by acylation.

The present invention is illustrated by but not intended to be limited to the following examples.

Example 1

To be able to carry out reactions in a glass microreactor from Corning, the microreactor has to allow or have modules for the following operations:
Production of an emulsion from the diol and dichloromethane.
Mixing of the diol/dichloromethane emulsion and nitric acid.
Residence modules which guarantee a sufficient residence time.

Examples 2 to 6

Mononitroesterification of 1,4-butanediol was carried out in capillary reactors, with the capillaries being either linear or being bent into a helical or zig-zag shapes. Dichloromethane was used as solvent with 85% strength nitric acid stabilized with 25 urea as nitrating agent. The molar ratio of HNO$_3$/BD was 15. the volume ratio of DCM/HNO$_3$ was 1. 20% NaOH in a molar ratio of NaOH/HNO$_3$ of 0.9 was used. The percentages by weight of 1,4-butanediol mononitrate and 1,4-butanediol dinitrate in the organic phase after neutralization are determined by means of gas chromatography. Results and conditions are summarized in Table 2 below.

Figure 1:
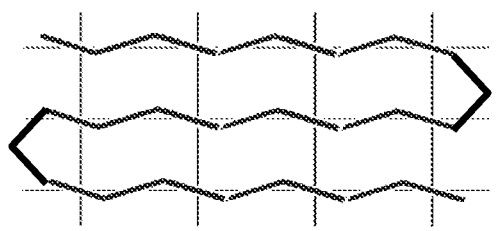
FIG. 1 depicts a mixing microreactor having a typical zig-zag arrangement of channels.
Figure 2:
FIG. 2 depicts a mixing microreactor having a helical arrangement of channels.
Figure 3:
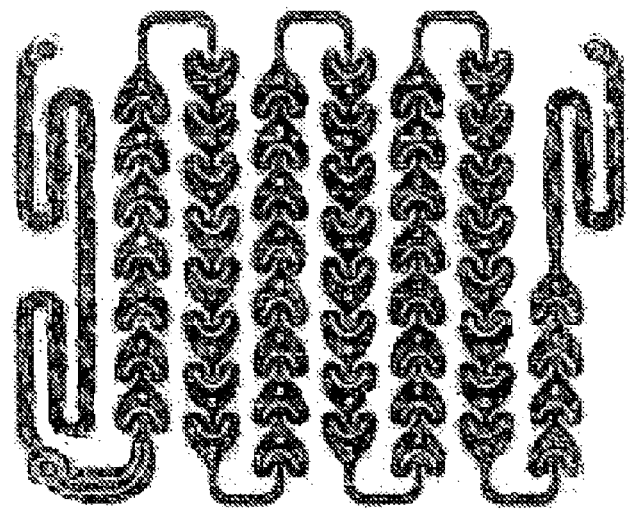
FIG. 3 depicts a mixing microreactor having a repeating heart-shaped motif. Such a microreactor is produced by Corning GmbH.

Mixing of the reagents, residence of the reaction mixture at a particular temperature for a particular time, dilution of the mixture and neutralization were realized in an arrangement (FIGS. 1 and 2) of circular cross-section capillaries bent into different shapes and T-pieces and the results were compared.

In the below table a pressure drop of 0.82 bar was recorded for Experiment 162, and a pressure drop of 1.14 bar was recorded for Experiment 127.

TABLE 2

Nitration of 1,4-butanediol in stainless steel capillaries bent into different shapes

| (Comp.) Example no. | Exp. no. | Mixing micro reactor 1 | | | | Process conditions | | |
|---|---|---|---|---|---|---|---|---|
| | | geometry | hydraulic diameter mm | length m | vol. ml | temp. °C | pressure Bar | res. time sec |
| C Ex 1 | 41 | L | 1.27 | 3.2 | 4.05 | 50 | 10 | 30 |
| C Ex 2 | 162 | L | 1.27 | 4.74 | 6 | 40 | 10 | 39 |
| Ex 2 | 127 | Z | 1.27 | 9.47 | 12 | 40 | 10 | 39 |
| Ex 3 | 186 | Z | 1.27 | 9.47 | 12 | 50 | 10 | 33 |
| Ex 4 | 199 | Z | 1.27 | 9.47 | 12 | 60 | 10 | 27 |
| Ex 5 | 125 | Z | 1.27 | 9.47 | 12 | 44 | 10 | 54 |
| Ex 6 | 159 | S | 1.27 | 4.74 | 6 | 40 | 10 | 39 |

| (Comp.) Example no. | Reactants | | | | | | Performance | | |
|---|---|---|---|---|---|---|---|---|---|
| | HNO3 | | 1,4-butanediol | | dichloromethane | | conv. | selectivity | selectivity |
| | conc. M % | flow ml/min | conc. M % | flow ml/min | conc. M % | flow ml/min | BD % | MN % | DN % |
| C Ex 1 | 80 | 2.54 | 90 | 0.47 | 100 | 5 | 72 | 25 | 1 |
| C Ex 2 | 85 | 4.33 | 90 | 0.57 | 100 | 4.33 | 100 | 40 | 32 |
| Ex 2 | 85 | 8.66 | 90 | 1.14 | 100 | 8.66 | 84 | 61 | 30 |
| Ex 3 | 85 | 9.93 | 90 | 1.96 | 100 | 9.93 | 51 | 80 | 9 |
| Ex 4 | 85 | 11.36 | 90 | 2.81 | 100 | 12.5 | 54 | 73 | 11 |
| Ex 5 | 85 | 5.07 | 90 | 0.67 | 100 | 7.6 | 100 | 40 | 60 |
| Ex 6 | 85 | 4.33 | 90 | 0.57 | 100 | 4.33 | 94 | 43 | 29 |

Abbreviations used in TABLE 2:
(Comp.) Ex: (Comparative) Example
Ex: Example
C Ex: Comparative Example
Exp. No.: Experiment no.
L: linear capilary channel
Z: zig zag capilary channel
S: spiral capilary channel (diameter of spiral of 4 mm)
vol.: volume
temp.: temperature
res. time: residence time
sec.: seconds
conc.: concentration
conv. BD: conversion of butanediol as % of starting butanediol
selectivity MN: mononitrate formed, as % of starting butanediol
selectivity DN: dinitrate formed, as % of starting butanediol

The invention claimed is:

1. A process for the continuous production of a compound of Formula (II), $$HO—R^1—ONO_2 \qquad (II)$$

wherein $R^1$ is a straight chain alkyl radical having from 3 to 6 carbon atoms, in a two-phase solvent system, comprising:
(a) forming the two-phase solvent system by contacting a compound of Formula (I), $$HO—R^1—OH \qquad (I)$$

wherein $R^1$ is as defined above, with nitric acid in the presence of first and second immiscible solvents,
(b) passing the two-phase solvent system under a flow condition through a mixing microreactor having an average hydraulic diameter and length to provide $\Delta W \geq 1.3 \Delta Ws$, wherein $\Delta W$ is a power loss of the reaction mixture flow at the flow condition through the mixing microreactor, and $\Delta Ws$ is a straight-channel power loss of the reaction mixture flow at the flow condition through a circular cross-section straight-channel microreactor having an internal diameter equal to the average hydraulic diameter of the mixing microreactor and a length equal to the length of the mixing microreactor; and
(c) in the mixing microreactor, continuously forming the compound of Formula (II) in the first solvent of the two-phase solvent system and extracting the formed compound of Formula (II) into the second solvent thereof.

2. A process according to claim 1, wherein step (b) is practiced such that $\Delta W \geq 2\Delta Ws$.

3. A process according to claim 1, wherein step (b) is practiced so that the two-phase solvent=system has a flow rate through the mixing microreactor of at least $0.1 ms^{-1}$.

4. A process according to claim 1, wherein the mixing microreactor has a zig-zag internal geometry.

5. A process according to claim 1, wherein the mixing microreactor comprises an internal geometry which is in a form of a repeating heart-shaped motif.

6. A process according to claim 1, wherein step (b) is practiced such that the flow condition of the two-phase solvent system through the mixing microreactor has a Reynolds number of from 400 to 2000.

7. A process according to claim 1, wherein the second solvent is a halogenated organic solvent.

8. A process according to claim 1, wherein the process is carried out at a temperature of from 30° C. to 60° C.

9. A process according to claim 1, wherein the compound of Formula (I) is 1,4-butanediol.

10. A process according to claim 1, further comprising the subsequent step of adjusting the two-phase solvent system to a pH of at least 7.

11. A process according to claim 1, wherein step (b) is practiced by passing the two-phase solvent system through more than one mixing microreactor in parallel.

* * * * *